United States Patent [19]

King et al.

[11] 4,016,867
[45] Apr. 12, 1977

[54] UTERINE CALIPER AND DEPTH GAUGE

[75] Inventors: Loyd L. King, Benton City; Robert G. Wheeler, Richland; Thomas M. Fish, Kennewick, all of Wash.

[73] Assignee: The United States of America as represented by the Secretary of the Department of Health, Education and Welfare, Washington, D.C.

[22] Filed: Apr. 27, 1976

[21] Appl. No.: 680,705

[52] U.S. Cl. .............................. 128/2 S; 33/174 D
[51] Int. Cl.² ........................................... A61B 5/10
[58] Field of Search ............ 128/2 S, 2 R, 361, 345; 33/174 D, 179

[56] References Cited

UNITED STATES PATENTS

| | | | |
|---|---|---|---|
| 512,025 | 1/1894 | Haviland | 33/174 D |
| 1,856,295 | 5/1932 | Sovatkin | 33/174 D X |
| 3,095,871 | 7/1963 | Mann et al. | 128/344 X |
| 3,630,190 | 12/1971 | Baker | 128/2 S |
| 3,706,307 | 12/1972 | Hasson | 128/2 S |
| 3,738,355 | 6/1973 | Salvatore | 128/2 S |
| 3,938,504 | 2/1976 | Oakes et al. | 128/2 S |

*Primary Examiner*—Kyle L. Howell
*Attorney, Agent, or Firm*—Browdy and Neimark

[57] ABSTRACT

A uterine caliper and sound consisting of an elongated body having outwardly biased resilient caliper wings and a spring-loaded slidable cervical stop. A slide on the body is operatively connected to the wings by a monofilament and operates with respect to a first scale on the body as a width indicator. A rod extending longitudinally on the body is connected to the cervical stop and cooperates with a second scale on the body as a depth indicator. The instrument can be positioned to measure the distance from the outer cervical ostium to the fundus, as read on said second scale. The wings may be allowed to open by moving the slide, and when the wings engage the utero-tubal junctions, the width may be read on said first scale. By adjustment of the caliper wings the instrument may be retracted until the resistance of the inner ostium of the cervix is felt, enabling the length of the cervical canal to be read directly by the position of the longitudinal indicator rod with respect to said second scale. The instrument may be employed to measure the width of the uterine cavity at any position between the inner ostium of the cervix and the fundus.

10 Claims, 7 Drawing Figures

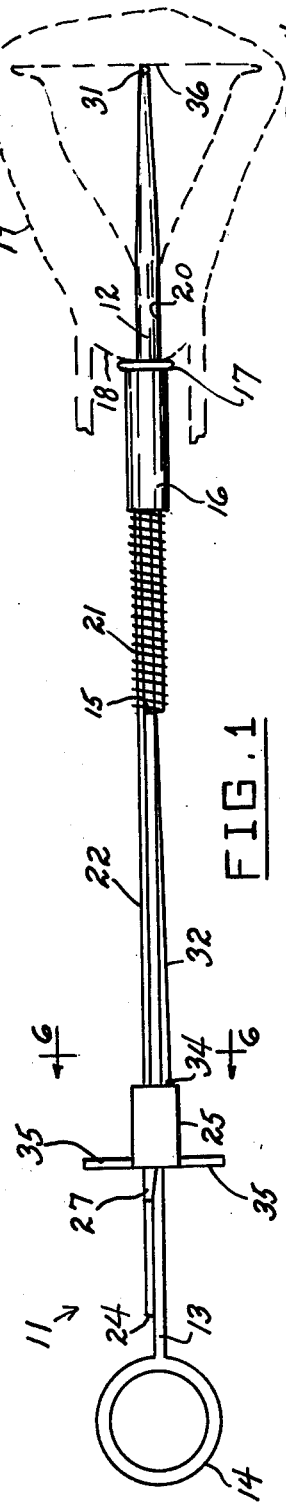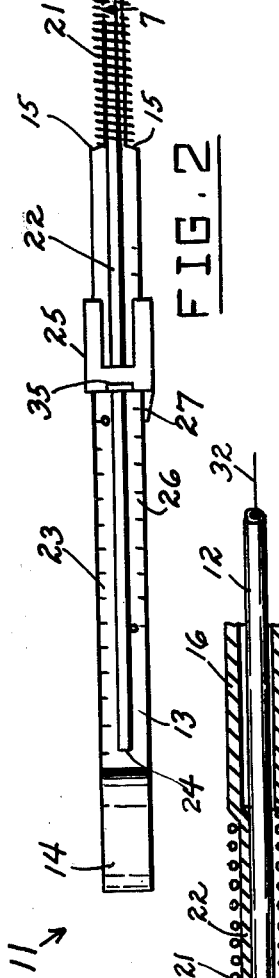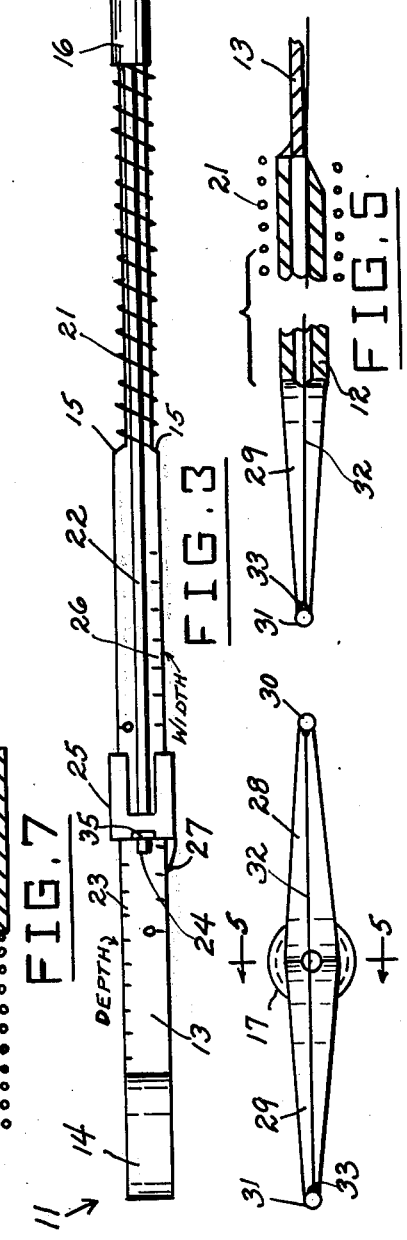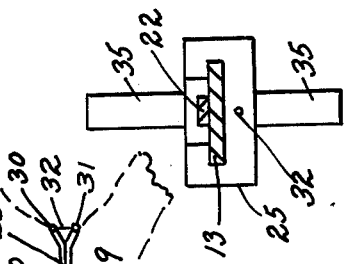

UTERINE CALIPER AND DEPTH GAUGE

FIELD OF INVENTION

This invention relates to gynecological instruments, and more particularly to an instrument for determining the size and shape of a uterine endometrial cavity, the length of the associated cervical canal, and other related uterine measurements.

BACKGROUND

In the practice of gynecology a need often arises to determine the size and shape of a uterine endometrial cavity, for example, in connection with the fitting of an intrauterine contraceptive device. The prior art has not provided a convenient instrument for determining the size and shape of an endometrial cavity.

In a typical wing sound of the prior art, laterally deployed wings are used, after the sound is inserted into the uterus, to sense the position of the inner ostium of the cervix, and thus determine by difference the distance between the inner ostium and the fundus. (See H. M. Hasson, "Differential Uterine Measurements Recorded in Vivo", *Obstetrics and Gynecology*, Vol. 43, No. 3, pp 400–412, March 1974). In order to determine the shape of the uterine cavity, in accordance with the prior art, it is necessary to fill the cavity with a radiopaque fluid, expose the patient to X-ray radiation, and produce a radiographic image of the cavity on film. This image does not provide accurate information because it is distorted in both magnification and shape by an amount which depends on the source object and image distances and on the orientation of the uterine cavity plane with respect to the plane of the X-ray film.

The U.S. Pat. No. 3,706,307 to Hasson discloses a gynecological instrument for use in measuring anatomical features of the cervical canal, isthmus and uterus, characterized by a shaft telescoped within a tube and connected to the distal end of the tube, with the tube being preferably formed of a pliable material and provided with spaced slits adjacent the free end thereof so that the relative retraction of the tube relative to the shaft forms laterally extending wings in the area of the slits. Numerical indicia are provided along the length of a body for the shaft. When the device is inserted through the cervical canal to the top of the uterus the entire depth of the cervical canal and endometrial cavity can be measured. When the tube is retracted relative to the shaft and then the entire assembly is retracted until the isthmus is located, the difference between the two dimensions may be measured, indicating the individual length of each of the cervical canal and the endometrial cavity. The wings 48a, 48b identify the position of the inner ostrium of the cervix (FIG. 6).

The Baker U.S. Pat. No. 3,630,190 discloses an intrauterine probe adapted to probe the cervical canal and uterus, at least one annular ridge 14 being provided for providing an indication of contact with the outer limit of the cervix. The U.S. Pat. No. 2,241,451 to Fist shows a gynecological instrument which has an expanding member for measuring body cavities, in particular a vaginal cavity, a distinguished from a uterine cavity. The U.S. Pat. No. 3,095,871 to Mann et al. is an example of a prior art radiological-balloon method of determining the shape of a uterine cavity. The United Kingdom Patent No. 141 of 1894 discloses an instrument for determining the limits of a body cavity, particularly a uterine cavity which includes radially extending tracing fingers 25 (FIG. 1).

There is an important need for an instrument which is free of distortion errors such as those above described, particularly in relation to the fitting of intrauterine contraceptive devices, so that the contraceptive device selected for a patient will more nearly correspond to the size and shape of the uterine cavity in which it is placed. There is substantial evidence that proper fitting of an intrauterine device to a uterine cavity will greatly reduced incidence of undesirable side effects caused by improperly fitted intrauterine devices. (See Hugh J. David and John Lesinski, "Uterine Variables in IUD Design", *Intrauterine Devices:* Development, Evaluation, and Program Implementation, R. G. Wheeler, G. W. Duncan, J. Joseph Speidel, editors, pp 91–96, 1974; S. Tejuja and P. K. Malkani, "Clinical Significance of Correlation Between the Size of the Uterine Cavity and the IUDC", *Am. J. Obstet. Gynec.* 105:620–627, 1969; Ibraham Kamal, M. Ghoneim, M. Talaat, M. Abdalla, "Retention and Expulsion of Intrauterine Contraceptive Devices", presented at the Population Council, Third International Conference on Intrauterine Contraception, Dec. 12–14, 1974).

SUMMARY

Accordingly, a prime purpose of the present invention is to fill this important need.

An object of the present invention is to overcome the deficiencies of the prior art, such as indicated above.

Another object is to provide for the improved fitting of intrauterine contraceptive devices.

A main object of the invention is to provide a novel and improved uterine caliper and sound which is relatively simple in construction, which is easy to operate, and which may be employed to accurately measure the depth of the uterus from the outer ostium of the cervix to the fundus, the length of the cervical canal, the depth from the inner ostium of the cervix to the fundus, the width of the uterus at the fundus, and the width of the uterine cavity at any position between the inner ostium of the cervix and the fundus.

A further object of the invention is to provide an improved uterine caliper device which can be employed to perform the above-described functions in a reliable and accurate manner and without requiring dilation of the cervix, which makes it possible to map the shape of the endometrial cavity, and which may be made in a curved form so that it is applicable to uteri in either the antiflexed or retroflexed position.

A still further object of the invention is to provide an improved uterine caliper device with the above-defined functional characteristics, which is relatively inexpensive to fabricate, which employs relatively few parts, which is durable in construction, and which is of great utility in the fitting of intrauterine contraceptive devices, so that such a device will more nearly correspond to the size and shape of a uterine cavity in which it is placed than has been feasible with previously employed means for measuring uterine cavities, and which will thereby reduce the incidence of undesirable side effects caused by improperly fitted intrauterine contraceptive devices.

The instrument of the present invention provides convenient and accurate measurements on a depth scale of the distance from the outer ostium of the cervix to the fundus, and the width of the uterus at the fundus on a width scale; in addition, with suitable adjustment the instrument may be retracted from the uterus until the resistance of the inner ostium of the cervix is felt. The length of the cervical canal can then be read directly from the depth scale; also, the instrument can be employed to measure the width of the uterine cavity at any position between the inner ostium and the fundus, thereby making it possible to map the complete interior shape of the endometrial cavity.

The instrument of the present invention employs an elongated uterine-insertable main body having resilient caliper end wings or jaws biased toward a normally open position, held in closed position by a width-indicating slide at the proximal end of the body. The width-indicating slide is actuated by the operator of the instrument, who is able to sense contact of the caliper wings or jaws with the lateral walls of the uterine cavity. This width-indicating slide is connected to the caliper wings or jaws by a flexible "monofilament" or cable which has the purpose of transmitting the "width" to the width-indicating slide and of reacting against the spring tension of the caliper wings or jaws so as to transmit any resistance encountered by the caliper wings or jaws to the fingers of the operator actuating the width-indicating slide. Thus, the instrument can be effectively employed to map the shape of the endometrial cavity.

BRIEF DESCRIPTION OF DRAWING

Further objects and advantages of the invention will become apparent from the claims, and from the following description of a specific embodiment as shown in the accompanying drawings, wherein:

FIG. 1 is a side elevational view of a typical uterine caliper device according to the present invention, shown in uterine depth-measuring position.

FIG. 2 is a top plan view, partly broken away, of the device of FIG. 1, shown in a position to measure uterine width at the fundus.

FIG. 3 is a top plan view similar to FIG. 2, showing the device in a position to measure the length of the cervical canal.

FIG. 4 is an enlarged end elevational view taken substantially on line 4—4 of FIG. 2.

FIG. 5 is a fragmentary cross-sectional view taken substantially on line 5—5 of FIG. 4.

FIG. 6 is an enlarged cross-sectional view taken substantially on line 6—6 of FIG. 1.

FIG. 7 is an enlarged cross-sectional view taken substantially on line 7—7 of FIG. 2.

DETAILED DESCRIPTION OF EMBODIMENT

Referring to the drawings, 11 generally designates a typical uterine caliper and sound constructed in accordance with the present invention. The device 11 comprises an elongated body having a tubular forward stem portion 12 and a somewhat widened flat bar-shaped rearward portion 13 integrally formed with a rear finger-engaging end ring 14. Abutment shoulders 15, 15 are thus defined at the junction of tubular forward stem portion 12 and flat bar member 13.

A cervical stop sleeve 16 receives and slidably engages on the tubular stem portion 12 and has a front bead or flange 17 engageable with the outer cervical ostium 18 of a typical uterus 19 when stem portion 12 is inserted through the cervical canal 20 thereof in the manner shown in FIGS. 1 to 3. A coiled spring 21 surrounds stem portion 12 and bears between shoulders 15, 15 and the rear rim of sleeve 16, biasing said sleeve rightwardly as viewed in FIGS. 1 to 3.

The rear end of sleeve 16 is formed with an inwardly offset longitudinally extending depth-indicating rod 22 which extends through coiled spring 21 and centrally overlies the flat bar element 13, as shown in FIGS. 2 and 7. The upper edge portion of bar element 13, as viewed in FIG. 2, is suitably inscribed with a uterine depth scale 23, and the end 24 of rod 22 is employed as an index element movable along scale 23 to provide a uterine cavity depth reading.

Slidably receiving flat bar element 13 and rod 22 and movable along said flat bar element is a width-indicating slide member 25. The lower edge portion of bar element 13, as viewed in FIG. 2, is suitably inscribed with a uterine width scale 26, and the slide member is provided with an index lug element 27 movable along scale 26 to provide a uterine width reading.

The forward end of stem portion 12 is suitably split and is formed with a pair of opposing resilient wings or jaws 28, 29 which are inherently biased away from each other toward spread-apart positions such as shown in FIG. 2. Said wings or jaws have smoothly rounded end feeler tips 30, 31. A flexible thin cable or monofilament 32 is suitably connected at its forward end to tip 30, passes through an eye loop 33 provided on wing 29 adjacent tip 31 (see FIGS. 4 and 5), extends through tubular stem portion 12 and under bar element 13, and is connected at its rear end to slide member 25, as shown at 34 in FIG. 1.

Slide member 25 is provided with a pair of opposing finger-engaging lugs 35, 35 oriented in a plane perpendicular to the axis of ring 14 for facilitating manual operation of the device. The slide member 25 has sufficient frictional engagement with bar element 13 to hold the wings or jaws in closed positions, as in FIG. 1, namely, to resist the spreading force acting on the wings or jaws 28, 29. The wings or jaws 28, 29 may be allowed to separate by manually moving slide member 25 rightwardly along bar element 13, as viewed in FIG. 1.

The diameter of stem member 20 is preferably relatively small, namely, of the order of 4 mm or less, enabling the instrument to be used on most patients without requiring dilation of the cervix. The wings or jaws 28, 29 are preferably forwardly tapered to facilitate insertion.

In using the device, the slide member 25 is placed in the position holding the wings or jaws 28, 29 closed, as in FIG. 1, and the instrument is inserted to the position of FIG. 1, with the stop flange 17 abutting the outer cervical ostium 18 and the feeler tips 30, 31 moved forwardly by bar element 13 until they are felt to engage the uterine fundus, shown at 36. The depth scale 23 is suitably calibrated so that in the position of FIG. 1 the distance between the outer cervical ostium 18 and the fundus 36 will be read by the position of rod tip 24 on scale 23.

To measure the uterine width at the fundus, the instrument is adjusted to the position of FIG. 2 with the slide member 25 manually moved rightwardly to release the caliper wings or jaws 28, 29 until the feeler tips 30, 31 are felt to engage at the utero-tubal junctions, as shown in FIG. 2. The width scale 26 is suitably calibrated so that in this position the width of the uterus at the fundus is indicated by index element 27 on width scale 26.

The length of the cervical canal 20 may be measured in the manner shown in FIG. 3 by setting the width (the distance between feeler tips 30, 31) to a predetermined value between ½ and 1 cm. The instrument is then retracted from the uterus until the resistance of the inner ostium of the cervix is felt. The length of the cervical canal is then read directly by rod tip 24 on depth scale 23. The distance from the inner cervical ostium to the fundus is the difference between the above first-obtained distance and the length of the cervical canal.

The distance from the inner ostium of the cervix to the fundus may be easily calculated from the above data. The width of the uterine cavity at any position between the inner ostium and the fundus can be readily measured by operating the slide member 25 so as to sense contact of the feeler tips 30, 31 with the lateral walls of the uterine cavity. Thus, by making a sufficient number of such measurements it is possible to map accurately the shape of the endometrial cavity.

The embodiment illustrated herein shows the instrument to be straight; however, within the spirit of the present invention it may be made in a curved form so that it is applicable to uteri in either the antiflexed or retroflexed position.

While a specific embodiment of an improved uterine caliper and sound has been disclosed in the foregoing description, it will be understood that various modifications within the spirit of the invention may occur to those skilled in the art. Therefore it is intended that no limitations be placed on the invention except as defined by the scope of the appended claims.

What is claimed is:

1. A uterine caliper and sound comprising an elongated body having a longitudinally split distal end and means to measure uterine width at the fundus comprising a pair of opposed outwardly resiliently biased caliper wings at said distal end, said wings constituting said split distal end, and said elongated body having a longitudinal scale portion, spring-loaded cervical stop means movably mounted on said body, depth indicator means rigidly connected to said cervical stop means and extending over said scale portion, width indicator means slidably mounted on said scale portion, and control means operatively interconnecting said width indicator means with said caliper wings to control the separation of said caliper wings in accordance with the position of said width indicator means on said scale portion and so that the wings can at times be closed for insertion into a uterus and can thereafter be released to internally engage the lateral walls of the uterus.

2. The uterine caliper and sound of claim 1, and wherein said control means comprises a flexible cable element interconnecting said slide element and said caliper wings.

3. The uterine caliper and sound of claim 2, and wherein said scale portion comprises a flat bar-like member having forward end shoulders.

4. The uterine caliper and sound of claim 3, and wherein said cervical stop means comprises a sleeve element slidably mounted on said body and spring means bearing between said shoulders and said sleeve element.

5. The uterine caliper and sound of claim 4, and wherein said depth indicator means comprises a longitudinally extending rod element rigidly secured to said sleeve element.

6. The uterine caliper and sound of claim 5, and wherein said width indicator means comprises a slide element receiving said bar-like member.

7. The uterine caliper and sound of claim 2, and wherein one of the caliper wings is provided with eye means and said flexible cable element passes through said eye means and is connected to the other caliper wing.

8. The uterine caliper and sound of claim 7, and wherein said elongated body has a tubular forward portion carrying said sleeve element and wherein said flexible cable element extends through said tubular forward portion.

9. The uterine caliper and sound of claim 8, and wherein said spring means comprises a coiled spring surrounding said tubular forward portion.

10. The uterine caliper and sound of claim 9, and wherein said scale portion is provided with a uterine depth scale at one longitudinal margin thereof and is provided with a uterine width scale at the opposite longitudinal margin thereof.

* * * * *